US006022940A

United States Patent [19]
Byerley et al.

[11] Patent Number: 6,022,940
[45] Date of Patent: Feb. 8, 2000

[54] POLYMERIC COMPOSITIONS AND COMPOSITES PREPARED FROM SPIROORTHOCARBONATES AND EPOXY MONOMERS

[75] Inventors: Thomas J. Byerley, Mission; Cecil C. Chappelow, Leawood; J. David Eick, Overland Park, all of Kans.

[73] Assignee: The Curators of the University of Missouri, Columbia, Mo.

[21] Appl. No.: 08/713,109

[22] Filed: Sep. 16, 1996

Related U.S. Application Data

[63] Continuation of application No. 08/085,981, Jul. 1, 1993, Pat. No. 5,556,896.

[51] Int. Cl.$^7$ .............................. C08L 63/00; C08L 69/00
[52] U.S. Cl. ......................... 528/103; 528/116; 528/418; 525/524
[58] Field of Search ................................... 528/103, 116, 528/418; 525/524

[56] References Cited

U.S. PATENT DOCUMENTS

| | | | |
|---|---|---|---|
| 4,368,314 | 1/1983 | Endo . | |
| 4,387,215 | 6/1983 | Bailey | 528/371 |
| 4,738,899 | 4/1988 | Bluestein et al. | 528/116 |
| 4,855,367 | 8/1989 | Flury et al. | 528/104 |

FOREIGN PATENT DOCUMENTS

| | | |
|---|---|---|
| 61-64726 | 4/1986 | Japan . |
| 64726 | 4/1986 | Japan . |

OTHER PUBLICATIONS

Anderson, et al., *Silicon Compounds: Register and Review*, 5th Edition, Piscataway, N.J., p. 4.

Phillips, *Science of Dental Materials*, 9th ed., pp. 215–233, 1991.

Byerley, et al., "Expandable Matrix Monomers for Dental Composites", *J. Dent. Res.* 69:263 Abstr. No. 1233; p. 263, Mar., 1990.

Byerley, et al., "Spiro–orthocarbonates: Polymerization and Volume Change Determinations", *J. Dent. Res.* 70:527, Abstr. No. 2087, p. 2087, Apr., 1991.

Byerley, et al., "Spiro–orthocarbonates: Polymerization and Volume Change Determinations", pp. 1–10, Apr., 1991.

William J. Bailey, "Matrices that Expand on Curing for High Strength Composites and Adhesives", *Materials Science & Engineering*, A126, pp. 271–279, (1990).

Bailey, et al., "Radical Ring–Opening Polymerization and Copolymerization with Expansion in Volume", *Journal of Polymer Science*: Polymer Symposium 64, pp. 17–26, (1978).

Stansbury, et al., "Evaluation of Spiro Orthocarbonate Monomers Capable of Polymerization with Expansion as Ingredients in Dental Composite Materials", *Progress in Biomedical Polymers*, pp. 133–139, 1990.

A.T. Blomquist, et al., "The Mineral Acid–catalyzed Reaction of Cyclohexene with Formaldehyde", *Acid–Catalyzed Reaction of Cyclohexene with Formaldehyde*, pp. 6025–6030, Nov. 20, 1957.

DeWolfe, "Synthesis of Carboxylic and Carbonic Ortho Esters", pp. 153–172, Mar., 1974.

Millich, et al., "Expansion Polymerization Density Change Determination", pp. 1–17.

M.A. Manzhen, *International Journal of Polymeric Materials*, "Photoinitated Cationic Copolymerization of an Alicyclic Epoxy Compound and a Spiroorthocarbonate", vol. 18, at pp. 1–7 (1992).

M.A. Manzhen, *International Journal of Polymeric Materials*, "Effect of Structural Difference of Photoinitiator on Photocopolymerization of an Alicyclic Epoxy Compound and a Spiroorthocarbonate", vol. 18, at pp. 189–195 (1992).

Pingsheng He; W. Zhou; G. Wang; C. Pan; and R. Wu, *Chinese Journal of Polymer Science*, "Study on Copolymer Epoxy Resin Matrix without Shrinkage: Part 1 Volume Change During Cure Processes", vol. 6, at pp. 30–35 (1988).

Pinsheng He and Zhiqiang Zhou, *Journal of Material Science*, "Epoxy Resin Copolymer with Zero Shrinkage, Part II Thermal and Mechanical Properties", vol. 26, at pp. 3792–3796 (1991).

Pingsheng He, et al., *Journal of Material Science*, "An Epoxy Resin Copolymer with Zero Shrinkage, Part I Volume Change on Cure", vol. 24, at pp. 1528–1532 (1989).

He et al., *Chem. Abs.*, 1099, Ab. #74,464 (1989).

Byerley et al., "Expandable Matrix Monomers For Dental Composites", pp. 1–9 (1990).

He et al., Chinese Journal of Polymer Science, vol. 6, No. 1, pp. 28–35 (1988).

He et al., J. Materials Sci., vol. 26, pp. 3792–3796 (1991).

He et al., J. Materials Sci., vol. 24, pp. 1528–1532 (1989).

Eick et al., Dent.Mater., vol. 9, pp. 123–127, Mar. 1993.

Byerly et al., Dent.Mater., vol. 8, pp. 345–350, Nov. 1992.

Byerly et al., J.Poly.Sci., Part B: Polym.Phys., vol. 31(6), pp. 729–733 (1993).

*Primary Examiner*—Donald R. Wilson
*Attorney, Agent, or Firm*—Shook, Hardy & Bacon

[57] ABSTRACT

Copolymer compositions are provided, including those which undergo less than ±1.0% bulk polymerization shrinkage and are useful as strain-free composites, high-strength adhesives, and precision castings. The copolymer compositions are formed from the cationic initiated polymerization of alicyclic spiroorthocarbonate monomers and epoxy resin monomers or comonomers. A preferred spiroorthocarbonate monomer is 2,3,8,9-di(tetramethylene)-1,5,7,11-tetraoxaspiro-[5,5]undecane. A preferred epoxy resin is a three component epoxy comonomer mixture of (i) diglycidyl ether of bisphenol A, (ii) 3,4-epoxycyclohexanemethyl-3,4-epoxycyclohexane carboxylate, and (iii) vinyl cyclohexene dioxide, preferably in a ratio of 5:4:1 by weight.

3 Claims, No Drawings

POLYMERIC COMPOSITIONS AND COMPOSITES PREPARED FROM SPIROORTHOCARBONATES AND EPOXY MONOMERS

This is a continuation of application Ser. No. 08/085,981 filed on Jul. 1, 1993, now U.S. Pat. No. 5,556,896.

BACKGROUND OF THE INVENTION

The government has certain rights in this invention.

This invention relates in general to compositions of matter and, more particularly, to novel copolymer compositions and products, including dental composites, made from such copolymer compositions.

The shrinkage during polymerization of many types of monomers makes those monomers generally unsuited for use in numerous applications, including as strain-free composites, high-strength adhesives, and precision castings. As an example, when such monomers are used in composites which include high-strength fibers, the polymeric matrix is subject to failure when the polymer shrinks and pulls away from the fibers. Failure of the composite can also occur when the matrix ruptures as a result of voids or microcracks which form in the matrix during polymerization shrinkage.

Polymeric matrices commonly employed in dental composites are based on 2,2'-bis[4-(2-hydroxy-3-methacryloyloxypropoxy)]phenyl propane (BisGMA). A significant problem associated with the use of this monomer in dental applications is the shrinkage which occurs as the monomer is polymerized. The BisGMA monomer itself typically experiences a shrinkage of approximately 5% and, when a low viscosity reactive diluent is combined with the monomer, the shrinkage may average as much as 7.9%. The adverse effects of such shrinkage are believed to include increased postoperative sensitivity, the formation of marginal gaps between the dental restoration and the cavity wall, cracking of the restoration, and microleakage and potential failure of the restoration.

The discovery that spiroorthocarbonates undergo reduced polymerization contraction has led to the suggestion of their use in reinforced composites, including as dental composites. Spiroorthocarbonates are esters of orthocarboxylic acid and have four oxygen atoms bonded to a single carbon atom, with the carbon atom being common to two ring systems. The expansion of the spiroorthocarbonates on polymerization is attributed to a double spiro-cyclic ring opening of the spiroorthocarbonates, resulting in the breaking of two covalent bonds to form one new bond.

Initial attempts to form a homogeneous polymer matrix from certain spiroorthocarbonates and BisGMA resin mixtures proved unsuccessful because of the incomplete polymerization of the spiroorthocarbonates. Thompson et al., *J. Dental Research* 58:1522–1532 (1979). More recent studies demonstrated that homogeneous mixtures of other spiroorthocarbonates and BisGMA could be obtained. Stansbury, *J. Dental Research* 70:527; Abstract No. 2088 (1991). However, the presence of a vinyl functionality in these spiroorthocarbonate monomers, in combination with the unsaturation of the BisGMA monomers, resulted in a polymerization shrinkage of 2.4%, making the polymer unsuited for those application requiring slight polymer expansion or minimal shrinkage.

The photocationic-initiated expansion polymerization of alicyclic spiroorthocarbonate monomers and the potential use of the resulting polymers as dental composites have been previously reported by the present inventors, with others. Byerley et al., *Dent. Mater.* 8:345–350 (1992). The specific spiroorthocarbonates identified by Byerley et al. include cis/cis, cis/trans, and trans/trans configurational isomers of 2,3,8,9-di(tetramethylene)-1,5,7,11-tetraoxaspiro-[5,5] undecane of the following (I):

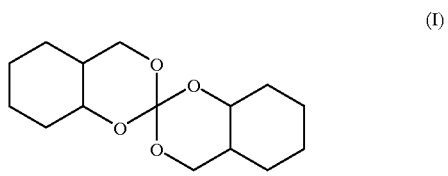

These spiroorthocarbonates were determined to undergo an expansion of 3.5% during homopolymerization and demonstrated acceptable cytotoxicity and genotoxicity properties, making them promising candidates as composite resin matrix materials.

The present inventors, with others, have also previously reported on the preparation of a copolymer of an alicyclic spiroorthocarbonate and an unidentified monofunctional epoxide, with the observation that there were no indications of the formation of small ring compounds as polymerization by-products. Byerley et al., *J. Dental Research* 69:263; Abstract No. 1233 (1990). The copolymerization of trans/trans-2,3,8,9-di(tetramethylene)-1,5,7,11-tetraoxaspiro-[5, 5]undecane and commercially available multifunctional epoxides was also disclosed in paper presented by Byerley et al. However, no physical or mechanical properties, including percentage shrinkage, of the copolymer compositions were disclosed.

The combination of other spiroorthocarbonates with epoxy resins have produced copolymer composite matrices exhibiting decreased water permeation, increased toughness, and significantly decreased polymerization shrinkage. In one example, an expansion of 1.6% was observed when 24% of a dinorbornene spiroorthocarbonate was copolymerized with a diglycidyl ether of bisphenol A. Piggott et al., *31st International SAMPE Symposium* 541–550 (1986).

It has also been reported that homopolymerization of an epoxy monomer at ambient temperature would result in very minimal shrinkage. Fish et al., *Plastic Technology,* 1:28–32 (1961).

Despite the advances resulting from the above-noted investigations of the use of spiroorthocarbonates as composite materials, a need still exists for a spiroorthocarbonate copolymer capable of yielding a hard, non-shrinking matrix resin suitable for formulating dental and other composites.

SUMMARY OF THE INVENTION

It is a primary object of this invention to provide a spiroorthocarbonate and epoxy copolymer composition that possesses the mechanical and physical properties necessary to allow the composition to be used as a composite material, including as a dental composite matrix.

It is also an object of this invention to provide a spiroorthocarbonate and epoxy copolymer composition that has a reduced polymerization shrinkage and water sorption in comparison to the epoxy polymer itself so that the copolymer composition can be used in those applications in which the epoxy polymer cannot be used.

It is another object of this invention to provide a dental composite resin matrix which has an acceptable water sorption so that the problems associated with absorption of water are avoided.

It is another object of this invention to provide a dental composite having a tensile strength and modulus of elasticity comparable with that of conventional dental composites but having negligible shrinkage during polymerization so that the composite is less likely to fail as a result of expansion or contraction during polymerization.

To accomplish these and other related objects of the invention, in one aspect the invention is related to a copolymer composition comprising a reaction product of a spiroorthocarbonate compound and a multifunctional epoxy resin, said spiroorthocarbonate compound having the formula (II):

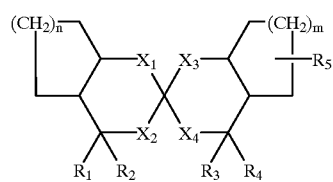

(II)

wherein m=1, 2, 3, or 4;

n=1, 2, 3, or 4;

$R_1$, $R_2$, $R_3$, and $R_4$ are independently selected from the group consisting of H, $CH_3$, $C_6H_5$, or perfluoroalkyl;

$R_5$ is H or perfluoroalkyl;

$X_1$, $X_2$, $X_3$, and $X_4$ are independently selected from the group consisting of O or S, with the proviso that when m and n=2, $R_{1-4}$=H, and $X_{1-4}$=O, the cationic initiated reaction product is characterized by the property of undergoing a bulk shrinkage of less than or equal to approximately ±1.0% during polymerization.

In another aspect, the invention is directed to a copolymer composition comprising a cationic initiated reaction product of an alicyclic spiroorthocarbonate compound and an epoxy resin, said cationic initiated reaction product being characterized by the property of undergoing a bulk shrinkage of less than or equal to approximately ±1.0% during polymerization.

In a further aspect, the invention is directed to a dental composite having a matrix comprising a cationic initiated reaction product of an alicyclic spiroorthocarbonate compound and an epoxy resin, said cationic initiated reaction product being characterized by the property of undergoing a bulk shrinkage of less than or equal to approximately ±0% during polymerization, and a filler comprising an inorganic material.

DESCRIPTION OF THE PREFERRED EMBODIMENTS

In accordance with the present invention, a copolymer composition is provided which is the cationic initiated reaction product of a spiroorthocarbonate monomer and an epoxy monomer. The copolymer can be characterized by the property of having a bulk polymerization shrinkage of less than or equal to approximately ±1.0%, and preferably less than or equal to approximately ±0.5%. The negligible shrinkage of the copolymer compositions of the present invention make them particularly suited for use as strain-free composites, high-strength adhesives, and precision castings, particularly in dental applications. Notably, the copolymer compositions exhibit low water sorption and the adverse effects of water sorption are thereby reduced.

The spiroorthocarbonate monomer used in the copolymer composition is preferably one or more alicyclic spiroorthocarbonate monomers of the formula (II):

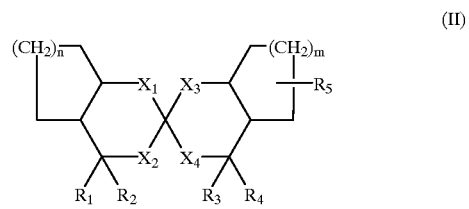

(II)

wherein m=1, 2, 3, or 4;

n=1, 2, 3, or 4;

$R_1$, $R_2$, $R_3$, and $R_4$ are independently selected from the group consisting of H, $CH_3$, $CH_6H_5$, or perfluoroalkyl;

$R_5$ is H or perfluoroalkyl;

$X_1$, $X_2$, $X_3$, and $X_4$ are independently selected from the group consisting of O or S, with the proviso that when m and n=2, $R_{1-4}$=H, and $X_{1-4}$=O, the cationic initiated reaction product is characterized by the property of undergoing a bulk shrinkage of less than or equal to approximately ±1.0% during polymerization.

In dental applications, the spiroorthocarbonate monomer must be selected in combination with the epoxy monomer so that the resulting copolymer undergoes a negligible shrinkage during polymerization. In other applications, greater shrinkage, including expansion as well as contraction, can be tolerated.

An example of spirorthocarbonate compounds encompassed within the invention are structural and optical isomers of the alicyclic spiroorthocarbonate 2,3,8,9-di(tetramethylene)-1,5,7,11-tetraoxaspiro-[5,5]undecane of the following formula (I):

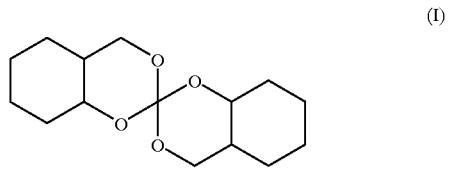

(I)

The structural and optical isomers may be used alone or in combination. Particularly preferred are the cis/cis, cis/trans, and trans/trans isomers of the compound of formula I, with the configurational nomenclature referring to the relationship of the cyclohexyl substituents H— and $OCH_2$— to each other on both of the cyclohexyl rings of the spiroorthocarbonate compound.

Other examples of suitable spiroorthocarbonates falling with the general formula II include:

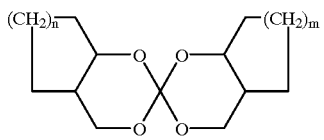

wherein n=1, and m=1 or 2;

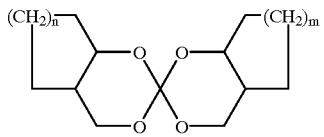

wherein n=4, and m=2 or 4;

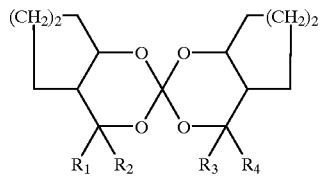

wherein $R_1=CH_3$ and $R_{2-4}=H$, $R_1=C_6H_5$ and $R_{2-4}=H$, $R_1=CH_3 R_4=CH_3$ and $R_{2-3}=H$, $R_1=CH_6H_5$, and $R_{2-3}=H$, or $R_{1-4}=CH_3$; and

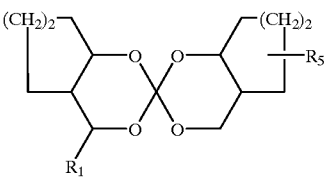

wherein $R_1$=perfluoroalkyl when $R_5$=H, and $R_5$=perfluoroalkyl when $R_1$=H;

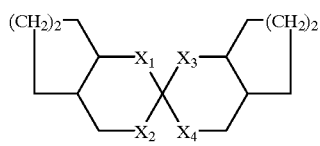

wherein one or more of $X_{1-4}$=S.

The spiroorthocarbonate compounds can be prepared by various methods, including by the classical Prins Reaction involving the formation of an intermediate diol by the acid catalyzed addition of olefins to formaldehyde, followed by acid-catalyzed transesterification of the diol to achieve the alicyclic spiroorthocarbonate. As an example, the 2,3,8,9-di (tetramethylene)-1,5,7,11-tetraoxaspiro-[5,5]undecane spiroorthocarbonates can be prepared from cis- and trans-2-hydroxymethyl cyclohexanol as illustrated below:

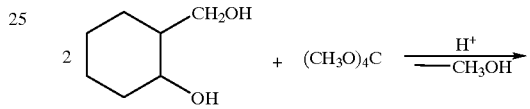

The resulting racemates are purified by vacuum distillation and fractional recrystallization.

The cis-2-hydroxymethyl cyclohexanol intermediate is preferably prepared by a two-step reduction of methyl salicylate as described by Blomquist et al. in *J. Amer. Chem. Soc.* 79:6025–6030 (1957), instead of by the Prins Reaction. The first step comprises the reduction of the aryl ring by low-pressure hydrogenation using Rh/C catalysis. The resulting methyl 2-hydroxyl cyclohexane carboxylate is then reduce using lithium aluminum hydride. The reaction scheme is illustrated below:

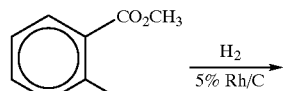

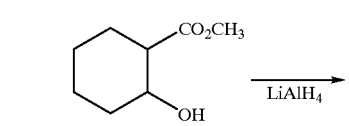

The trans-2-hydroxymethyl cyclohexanol intermediate can be prepared by the classical Prins Reaction using acid-catalyzed condensation of formaldehyde with cyclohexene, as characterized by Blomquist et al. in *J. Amer. Chem. Soc.* 79:6025–6030 (1957) and illustrated below:

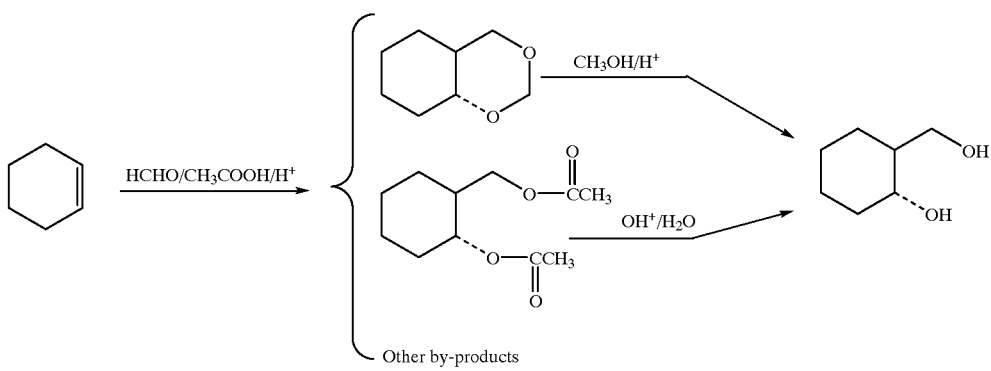

The epoxy monomer is preferably multifunctional and is chosen to provide a low viscosity fluid reaction mass in which the spiroorthocarbonates described above are soluble, including at loading concentrations of up to or exceeding 50% by weight. The epoxy resin should also cure rapidly at ambient temperature. As a general rule, an average epoxy value (defined as the number of epoxy groups per 100 grams of epoxy resin) of greater than 0.5 is necessary to achieve a rapid ambient cure.

One example of a suitable epoxy monomer or resin in accordance with the present invention comprises a three component epoxy comonomer mixture of (i) diglycidyl ether of bisphenol A, (ii) 3,4-epoxycyclohexanemethyl-3,4-epoxycyclohexane carboxylate, and (iii) vinyl cyclohexene dioxide, preferably in a ratio of 5:4:1 by weight. The epoxy value of this mixture is 0.703, based on the weight percentage of each monomer present in the mixture.

The diglycidyl ether of bisphenol A epoxy monomer is represented by the formula (VIII):

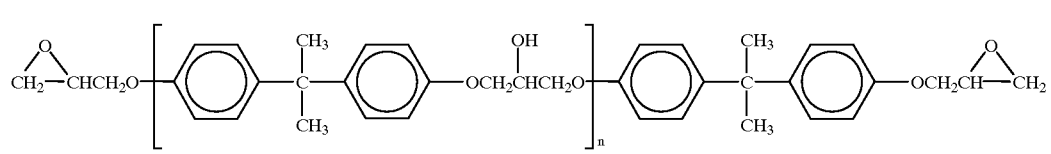

and has an epoxy equivalent of 185, a viscosity of 5000–6000 centipoises, and is commercially available from Ciba Geigy under the brand designation 6004.

The 3,4-epoxycyclohexanemethyl-3,4-epoxycyclohexane carboxylate epoxy monomer of formula (IX):

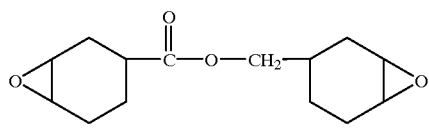

has an epoxy equivalent of 133 and a viscosity of 350–450 centipoises and is available from Union Carbide under the brand designation ERL 4221.

The vinyl cyclohexene dioxide epoxy monomer used in the epoxy comonomer mixture has the formula (X):

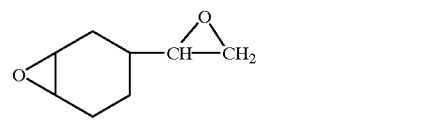

and an epoxy equivalent of 76, a viscosity of 20 centipoises and is available from Ciba Geigy under the brand designation RD-4.

The polymerization of the spiroorthocarbonate monomer and epoxy monomer/comonomer mixture can be initiated by any suitable catalyst which will cause cationic rather than free radical initiation of the polymerization. A preferred catalyst is a light initiated cationic catalyst such as (4-octyloxyphenyl)phenyl-iodonium hexafluoroantimonate, which is commercially available. A photosensitizer such as 2-chlorothioxanthen-9-one can be used to extend the spectral sensitivity of the photoinitiator to longer wavelengths. Desirably, the photoinitiator should be sensitized to the visible spectrum to allow the polymerization to be initiated at room temperature using visible light.

The polymerization of the spiroorthocarbonate monomer and epoxy monomer/comonomer mixture is initiated by adding suitable amounts of the photoinitiator and the optional sensitizer to the mixture and activating the initiator by exposure to a suitable light source. As one example, a photoinitiator comprising (4-octyloxyphenyl) phenyl-iodonium hexafluoroantimonate dissolved in methanol is added to the monomer/comonomer reaction mixture at a concentration level of 2 mole percent, and a photosensitizer comprising 2-chlorothioxanthen-9-one dissolved in methylene chloride is added to the reaction mixture at a concentration level of 0.2 mole percent. The reactants are then mixed by a suitable mixer to form a homogenized mixture which is then subjected to high vacuum to remove entrapped air and the majority of the volatile methanol and methylene chloride solvents introduced with the photoinitiator and photosensitizer. Removal of the volatile solvents is necessary to prevent shrinkage of the polymers during polymerization as a result of loss of the low molecular weight solvents.

Following application of the high vacuum, the reaction mixture is light activated by exposure to a light source such as a 275-watt high-intensity broad spectrum sun lamp. As previously mentioned, it is desirable in some applications to use a photoinitiator which will cause the polymerization to occur upon exposure to visible light.

The copolymer compositions of the present invention have utility as composites and in other applications. Notably, the lack of volume contraction and, in some instances, a slight expansion during polymerization make the copolymer compositions particularly useful in dental applications, such as for dental fillings, precision castings, and strain-free composite matrix resins.

Filler particles can optionally be blended with the alicyclic spiroorthocarbonate and multifunctional copolymer composition to form a composite resin matrix for dental applications. The filler particles can be made of any suitable material but typically are inorganic in nature. Among the properties to be considered in selecting a filler are desired filler volume level, particle size, particle size distribution, index of refraction, radiopacity and hardness. Silicone dioxide is one example of a suitable filler. The filler particles can be produced by grinding or milling a material such as quartz or glass to an acceptable size, such as from 0.02 $\mu$m to 100 $\mu$m. A range of particles sizes is typically used to increase the amount of loading of filler material in the resin matrix.

The amount of filler which can be added to the copolymer composition is dependent upon the total surface area of the filler particles. If colloidal size particles in the range of 0.02 to 0.04 $\mu$m are used, addition of a little as 5% by weight of the particles will be sufficient to modify the viscosity of the copolymer. Desirably, the filler can be present in an amount of between 20% and 80% by weight.

In order to increase the strength of the composite, a coupling agent can be used to increase the bonding strength of the copolymer to the filler particles. This enhanced bonding can improve the physical and mechanical properties of the composite and can provide hydrolytic stability by preventing water from penetrating along the interface between the copolymer and the filler.

A coupling agent should be chosen which is compatible with the copolymer and filler and will not significantly contribute to shrinkage of the composite during polymerization. Organosilanes are generally suitable coupling agents and commercially available 3-glycidoxypropyltrimethoxysilane is a preferred coupling agent when silicone dioxide is used as the filler material.

The following examples are intended to illustrate the invention are not to be construed in a limiting sense.

EXAMPLE 1

A three component epoxy comonomer was prepared comprising a mixture of (i) diglycidyl ether of bisphenol A, (ii) 3,4-epoxycyclohexanemethyl-3,4-epoxycyclohexane carboxylate, and (iii) vinyl cyclohexene dioxide, in a ratio of 5:4:1 by weight. Four combinations of the epoxy comonomer with trans/trans-2,3,8,9-di(tetramethylene)-1,5,7,11-tetraoxaspiro-[5,5]undecane (SOC) were then blended: (i) epoxy comonomer with 0 wt % trans/trans SOC, (ii) epoxy comonomer with 5 wt % trans/trans SOC, (iii) epoxy comonomer with 15 wt % trans/trans SOC, and (iv) epoxy comonomer with 30 wt % trans/trans SOC. The blended copolymer compositions were cured to a hard, brittle, transparent, yellowish state and then tested for tensile strength, modulus of elasticity, water sorption and solubility.

The tensile strength (MPa) and modulus of elasticity (GPa) were determined according to ASTM D638 (1991) using between six and ten micro tensile test specimens of each experimental formulation. The dimensions of the micro tensile test specimens were: width=2.0 mm; thickness=2.0 mm; and gauge length=12.0 mm. The results are presented in Table 1.

TABLE 1

| Test Material | Tensile Strength (MPa) | Modulus of Elasticity (GPa) |
|---|---|---|
| I (0% SOC) n = 9 | 39 +/− 12 | 2.0 +/− 0.7 |
| II (5% SOC) n = 6 | 29 +/− 18 | 2.2 +/− 0.5 |
| III (15% SOC) n = 8 | 48 +/− 9 | 2.8 +/− 0.4 |
| IV (30% SOC) n = 10 | 34 +/− 4 | 2.0 +/− 0.4 |

The results presented in Table 1 demonstrate that the copolymer compositions of the present invention exhibit tensile strength and modulus of elasticity values comparable to conventional unfilled matrix resins. Notably, the copolymer compositions show statistical equivalence to the epoxy comonomer control (0% SOC) using a one-way analysis of variance (ANOVA) with p <0.01.

EXAMPLE 2

The four combinations of the epoxy comonomer with trans/trans-2,3,8,9-di(tetramethylene)-1,5,7,11-tetraoxaspiro-[5,5]undecane (SOC) as set forth in Example 1 were tested for water sorption and solubility in the manner specified in ISO 4049 (1988). The results are set forth in Table 2.

TABLE 2

| Test Material | Water Sorption ($\mu$g/mm$^3$) | Water Solubility ($\mu$g/mm$^3$) |
|---|---|---|
| I (0% SOC) | 45 | −9 |
| II (5% SOC) | 46 | −4 |
| III (15% SOC) | 60 | 6 |
| IV (30% SOC) | 65 | 75 |

These results demonstrate that the epoxy control and copolymer containing 5% SOC possess acceptable water sorption and water solubility. The remaining materials exceeded the test limits of 50 $\mu$m/mm$^3$ and 5 $\mu$g/mm$^3$ for water sorption and water solubility, but it is believed that these results were due to a lack of complete cure of the copolymer composition.

EXAMPLE 3

The volume expansion of the four combinations of the epoxy comonomer with trans/trans-2,3,8,9-di(tetramethylene)-1,5,7,11-tetraoxaspiro-[5,5]undecane (SOC) of Example 1 were determined using the following relationship:

$$\text{percentage shrinkage} = \frac{d_{copolymer} - d_{monomer}}{d_{copolymer}} \times 100$$

where d=density.

The density of the resulting copolymers was determined using a water displacement technique in accordance with ASTM D792 (1991). In general, the test specimens were placed in a pycnometer covered with water and trapped surface bubbles were removed with vacuum. The density was determined rapidly after placement in the pycnometer in order to minimize water sorption.

The density of the uncured monomer mixtures was determined from the molar volume in dilute solution, using a technique described by Millich et al. in *J of Polymer Science: Part B. Polymer Physics* 31:729–733, which is incorporated herein by reference.

The results of the density determinations and percentage shrinkage are set forth in Table 3.

TABLE 3

| Test Material | Shrinkage | $d_{monomer}$ | $d_{copolymer}$ |
| --- | --- | --- | --- |
| I (0% SOC) | +0.3 | 1.2101 | 1.2130 |
| II (5% SOC) | −0.1 | 1.2053 | 1.2043 |
| III (15% SOC) | −0.8 | 1.1951 | 1.1868 |
| IV (30% SOC) | −0.4 | 1.1980 | 1.1926 |

The negative shrinkage values correspond to expansion of the copolymer composition, with all three formulations containing SOC demonstrating slight expansion during polymerization at ambient temperature. By contrast, the epoxy control contracted during polymerization.

The resulting copolymers were then extracted using 1,1,2-trichloroethylene to determine the degree of copolymerization which had been achieved. Infrared spectra and gas chromatography of the soluble copolymers indicated that the extractables were not SOC monomers or homopolymers but were low molecular weight copolymers. Gel permeation chromatography showed that the molecular weights were between 2000 and 3000, with a degree of polymerization of 8–10 monomer units. Notably, infrared spectroscopy of the copolymer mixtures showed no evidence of any residual SOC or epoxy monomers.

Having thus described the invention, what is claimed is:

1. A copolymer composition comprising a cationic initiated reaction product of 2,3,8,9-di(tetramethylene)-1,5,7,11-tetraoxaspiro-[5,5]-undecane and a multifunctional epoxy resin comprised of an epoxy comonomer mixture of (i) diglycidyl ether of bisphenol A, (ii) 3,4-epoxycyclohexanemethyl-3,4-epoxycyclohexane carboxylate, and (iii) vinyl cyclohexene dioxide, in a ratio of approximately 5:4:1 by weight, said cationic initiated reaction product being characterized by the property of undergoing a bulk shrinkage of less than or equal to approximately ±1.0% during polymerization.

2. The copolymer composition as set forth in claim 1, wherein said cationic initiated reaction product is characterized by the property of undergoing a bulk shrinkage of less than or equal to approximately ±0.5% during polymerization.

3. The copolymer composition as set forth in claim 1, wherein said 2,3,8,9-di(tetramethylene)-1,5,7,11-tetraoxaspiro-[5,5]undecane is trans/trans 2,3,8,9-di(tetramethylene)-1,5,7,11-tetraoxaspiro-[5,5]undecane.

* * * * *